(12) United States Patent
Feng et al.

(10) Patent No.: US 11,735,319 B2
(45) Date of Patent: Aug. 22, 2023

(54) METHOD AND SYSTEM FOR PROCESSING MEDICAL DATA

(71) Applicant: Beijing Tsinghua Changgung Hospital, Beijing (CN)

(72) Inventors: Xiaobin Feng, Beijing (CN); Chengquan Li, Beijing (CN); Meilong Wu, Beijing (CN); Jiahong Dong, Beijing (CN)

(73) Assignee: BEIJING TSINGHUA CHANGGUNG HOSPITAL, Beijing (CN)

( * ) Notice: Subject to any disclaimer, the term of this patent is extended or adjusted under 35 U.S.C. 154(b) by 0 days.

(21) Appl. No.: 17/954,650

(22) Filed: Sep. 28, 2022

(65) Prior Publication Data
US 2023/0094564 A1   Mar. 30, 2023

(30) Foreign Application Priority Data

Sep. 29, 2021  (CN) .......................... 202111147495.7

(51) Int. Cl.
*G16H 40/63* (2018.01)
*G06F 21/60* (2013.01)

(52) U.S. Cl.
CPC ........... *G16H 40/63* (2018.01); *G06F 21/602* (2013.01)

(58) Field of Classification Search
CPC ....... G16H 40/63; G06F 21/602; G06F 21/31; G06F 21/6245
See application file for complete search history.

(56) References Cited

FOREIGN PATENT DOCUMENTS

| CN | 109960944 A | 7/2019 |
|---|---|---|
| CN | 10688662 A | 1/2020 |

*Primary Examiner* — Abiy Getachew
(74) *Attorney, Agent, or Firm* — WPAT, PC (57) ABSTRACT

A method and a system for processing medical data are provided. The method executed by a first device and a second device includes: the first device performs desensitization processing on first medical data in a first secure working environment to obtain desensitized data, provides the desensitized data to the second device; the desensitization processing is preset in the first secure working environment, and the first medical data is stored in the first secure working environment; the second device performs restoration processing on the desensitized data in a second secure working environment to obtain the first medical data, the restoration processing is preset in a second secure working environment, and the restoration processing corresponds to the desensitization processing.

7 Claims, 4 Drawing Sheets

| Name | Age | ID card number | Address | Medical institution | Symptom |
|---|---|---|---|---|---|
| Zhang San | 56 | 101122196501022537 | No. 6 Huayuan Road, Haidian District, Beijing | Neurosurgery, Third Hospital of Peking University | Neurasthenia |

FIG. 3A

| Name | Age | ID card number | Address | Medical institution | Symptom |
|---|---|---|---|---|---|
| Zhang San | 56 | 10XXXX19650 1022537 | No. X, XX, XX, Beijing | Neurosurgery, Third Hospital of Peking University | Neurasthenia |

FIG. 3B

Performing desensitization processing on first medical data in a first secure working environment to obtain desensitized data, where the desensitization processing is preset in the first secure working environment, and the first medical data is stored in the first secure working environment — 410

Providing the desensitized data to a second device — 420

FIG. 4

Obtaining desensitized data in a second secure working environment, where the desensitized data is data obtained after first medical data is desensitized — 510

Performing restoration processing on the desensitized data to obtain the first medical data, where the restoration processing is preset in the second secure working environment, and the restoration processing corresponds to the desensitization processing — 520

METHOD AND SYSTEM FOR PROCESSING MEDICAL DATA

TECHNICAL FIELD

The disclosure relates to the field of data security technologies, and more particularly to a method for processing medical data and a system for processing medical data.

BACKGROUND

Medical data contains a large amount of sensitive data, such as personal information, medical information, disease information, past medical history data, and other data about personal privacy. In the conventional medical working environment, the sensitive data in medical data is generally protected by data encryption to avoid its leakage.

However, protecting sensitive data in medical data by means of data encryption results in poor portability of the medical data. In addition, since encrypted medical data needs to be decrypted by a corresponding key, in order to protect the sensitive data therein, it is necessary to effectively manage the corresponding key to avoid its loss or leakage. If the corresponding key is not managed properly, the risk of sensitive data leakage will be increased to a certain extent.

Therefore, an improved scheme to protect sensitive data and realize flexible application of data is desired.

SUMMARY

One or more embodiments of the disclosure provide a method for processing medical data and a system for processing medical data, so as to protect sensitive data and realize flexible application of data.

In a first aspect, there is provided a method for processing medical data, executed by a first device and a second device, including:

performing, by the first device, desensitization processing on first medical data in a first secure working environment to obtain desensitized data, and then providing, by the first device, the desensitized data to the second device; the desensitization processing being preset in the first secure working environment, and the first medical data being stored in the first secure working environment; and performing, by the second device, restoration processing on the desensitized data in a second secure working environment to obtain the first medical data; the restoration processing being preset in the second secure working environment, and the restoration processing corresponding to the desensitization processing.

In an embodiment, the method further includes: encrypting, by the first device, the desensitized data using a first key preset in the first secure working environment after obtaining the desensitized data, to obtain encrypted desensitization data;

the providing the desensitized data to the second device includes: providing the encrypted desensitization data to the second device; and decrypting, by the second device, the encrypted desensitization data using a second key preset in the second secure working environment to obtain the desensitized data.

In an embodiment, the providing the desensitized data to the second device includes after storing the desensitized data in the mobile storage device, providing the desensitized data to the second device through the mobile storage device; and the first device and the second device are configured (i.e., structured and arranged) to be capable of running a driver of the mobile storage device only through the first secure working environment and the second secure working environment respectively.

In an embodiment, the method further includes that the first device is configured to start the first secure working environment when the first device is powered on to set the first device interface under the first secure working environment, the second device is configured to start the second secure working environment when the second device is powered on to set a second device interface under the second secure working environment, thereby the first device and the second device are capable of running a driver of the mobile storage device only through the first secure working environment and the second secure working environment respectively.

In an embodiment, the method further includes performing identity authentication, by the first device, on the mobile storage device before the storing the desensitized data in the mobile storage device.

In an embodiment, the performing, by the first device, desensitization processing on the first medical data in the first secure working environment includes:

extracting, by the first device, sensitive data from the first medical data; and performing, by the first device, the desensitization processing on the sensitive data.

In an embodiment, the method further includes: reading, by the second device, the desensitized data from the mobile storage device after determining a login account having a permission to read the mobile storage device in the second secure working environment.

In a second aspect, there is provided another method for processing medical data, executed by a first device, including:

performing desensitization processing on first medical data in a first secure working environment to obtain desensitized data, the desensitization processing being preset in the first secure working environment, and the first medical data being stored in the first secure working environment; and providing the desensitization data to a second device.

In a third aspect, there is provided further another method for processing medical data, executed by a second device, including:

obtaining desensitized data in a second secure working environment, and the desensitization data being data obtained after the first medical data is performed desensitization processing; and performing a restoration processing on the desensitized data to obtain the first medical data, the restoration processing being preset in the second secure working environment, and the restoration processing corresponding to the desensitization processing.

In a fourth aspect, there is provided a system for processing medical data, including a first device and a second device;

the first device is configured to perform desensitization processing on first medical data in a first secure working environment to obtain desensitized data, and provide the desensitized data to the second device, the desensitization processing is preset in a first secure working environment, and the first medical data is stored in the first secure working environment; and the second device is configured to perform restoration processing on the desensitized data in a second secure working environment to obtain the first medical data, the restoration processing is preset in the second secure working environment, and the restoration processing corresponds to the desensitization processing.

In a fifth aspect, there is provided an apparatus for processing medical data, provided in a first device, the apparatus includes:

a desensitization module, configured to perform desensitization processing on first medical data in a first secure working environment to obtain desensitized data, the desensitization processing being preset in the first secure working environment, and the first medical data being stored in the first secure working environment; and a data transmission module, configured to provide the desensitized data to a second device.

In a sixth aspect, there is provided an apparatus for processing medical data, provided in a second device, the apparatus includes:

a data obtaining module, configured to obtain desensitized data in a second secure working environment, the desensitization data being data obtained after the first medical data is performed desensitization processing; and a data restoration module, configured to perform restoration processing on the desensitized data to obtain the first medical data, the restoration processing being preset in the second secure working environment, and the restoration processing corresponding to the desensitization processing.

In a seventh aspect, there is provided a computer-readable storage medium, including computer programs stored thereon, and the computer programs are configured to be executed in a computer to make the computer to execute the method according to the second aspect.

In an eighth aspect, there is provided a computing device, including a memory and a processor, executable codes are stored in the memory, and the processor is configured to execute the executable codes to implement the method according to the second aspect.

In a ninth aspect, there is provided a computer-readable storage medium, including computer programs stored thereon, and the computer programs are configured to be executed in a computer to make the computer to execute the method according to the third aspect.

In a tenth aspect, there is provided a computing device, including a memory and a processor, executable codes are stored in the memory, and the processor is configured to execute the executable code to implement the method according to the third aspect.

According to the method and the system provided in the embodiments of the disclosure, the first device performs the desensitization processing on the first medical data stored in the first secure working environment by using the desensitization processing preset in the first secure working environment to obtain the desensitized data, and provides the desensitized data to the second device. The second device performs the restoration process on the desensitized data by using the restoration process preset in the second secure working environment to obtain the first medical data. After the sensitive data of the first medical data is hidden and desensitized, the sensitive data is transmitted between the first device and the second device, and the desensitization processing and the restoration process are respectively preset in the first secure working environment of the first device and the second secure working environment of the second device. In this situation, the desensitization processing and the restoration processing do not require human intervention, which realizes the protection of the sensitive data, improves the data portability within a certain range, and realizes the flexible application of the data to a certain extent.

BRIEF DESCRIPTION OF DRAWINGS

In order to explain technical solutions of embodiments of the disclosure more clearly, the following will briefly introduce the drawings required in the description of the embodiments. Apparently, the drawings in the following description are only some embodiments of the disclosure. For those skilled in the art, other drawings can be obtained from these drawings without creative labor.

DETAILED DESCRIPTION OF EMBODIMENTS

Technical solutions of illustrated embodiments of the disclosure will be described in detail below with reference to the accompanying drawings.

The illustrated embodiments of the disclosure provide a method for processing medical data. Application scenarios and an inventive concept of the method for processing medical data are described as follows.

At present, the protection of sensitive data in medical data is generally in the form of encryption or physical isolation. When the sensitive data in the medical data is protected in the form of encryption, the medical data needs to be decrypted through a corresponding key when decrypting the medical data. In order to protect the security of medical data, the management of the key is critical. If the relevant key is not managed properly, such as lost or leaked, the risk of sensitive data leakage will be increased to a certain extent, and the portability of medical data will be reduced to a certain extent. When the sensitive data is protected in the form of physical isolation, the data flow between the device where the medical data is located and its external equipment needs to be limited, which increases the cost to a certain extent and reduces the flexibility of medical data application.

Figure 1:
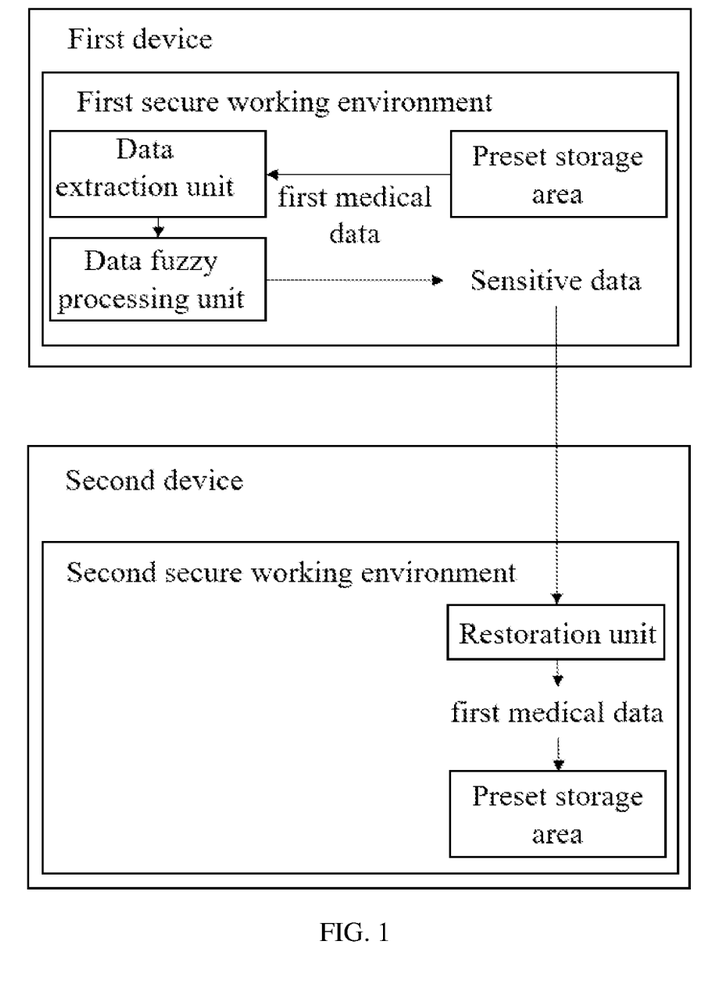
FIG. 1 illustrates a schematic diagram showing an implementation framework according to an embodiment of the disclosure.

In view of this, an embodiment of the disclosure provides a method for processing medical data, which is executed by a first device and a second device. As shown in FIG. 1, a schematic diagram showing an implementation framework according to an embodiment of the disclosure is illustrated. The first device performs desensitization process on first medical data by using a started data extraction unit and a started data fuzzy processing unit in a first secure working environment to obtain desensitized data. The data extraction unit is used to extract sensitive data from the first medical data, and the data fuzzy processing unit is used to perform fuzzy processing, that is, desensitization processing, on the sensitive data extracted by the data extraction unit. The first device provides the desensitized data to the second device, the desensitization processing is preset in the first secure working environment, and the first medical data is stored in the first secure working environment.

The second device performs restoration processing on the desensitized data to obtain the first medical data by using a started restoration unit in a second secure working environment, the restoration processing is preset in the second secure working environment, and the restoration processing corresponds to the desensitization processing.

The first medical data may be stored in a preset storage area in the first secure working environment of the first device. After the second device obtains the first medical data, the first medical data may be stored in a preset storage area in the second secure working environment.

In this embodiment, the "first" of the first secure working environment and the "second" of the second secure working environment are only to distinguish secure working environments set in different devices, and do not have other limiting meanings. The secure working environment may be a general term for the first secure working environment of the first device and the second secure working environment of the second device.

The first device and the second device each are disposed with the secure working environment, the secure working environment may be implemented by security sandbox technology, virtual secure desktop technology, or virtual working environment created based on an embedded system.

In one implementation, the first device and the second device may be devices in the same intranet, and accordingly, the first device may provide the desensitized data to the second device through the intranet. In another implementation, the first device and the second device may run drivers of device interfaces set by them in their secure working environment, that is, the first device may provide the desensitized data to the second device through a mobile storage device in the first secure working environment. The second device may perform restoration processing on the desensitized data in the second secure working environment, to obtain plaintext of the first medical data, so as to realize the sharing of the first medical data within a certain range and realize the flexible application of the first medical data.

In one implementation, it is determined that data needs to be provided to outside in the second secure working environment, the second device may start the data extraction unit and the data fuzzy processing unit to perform desensitization processing on the medical data stored locally or in a connected storage device of the second device, and then provide the desensitized medical data to the outside. The first device may also perform restoration processing on the desensitized medical data obtained from the outside in the first secure working environment.

In this embodiment, the sensitive data of the first medical data is transmitted between the first device and the second device after being hidden and desensitized, and the desensitization processing and the restoration processing are preset in the secure working environment of the devices. The desensitization processing and the restoration processing do not require human intervention, which realizes the protection of sensitive data, improves the portability of medical data within a certain range, and realizes the flexible application of data to a certain extent.

The method for processing medical data provided in the disclosure is described in detail below in combination with specific embodiments.

Figure 2:
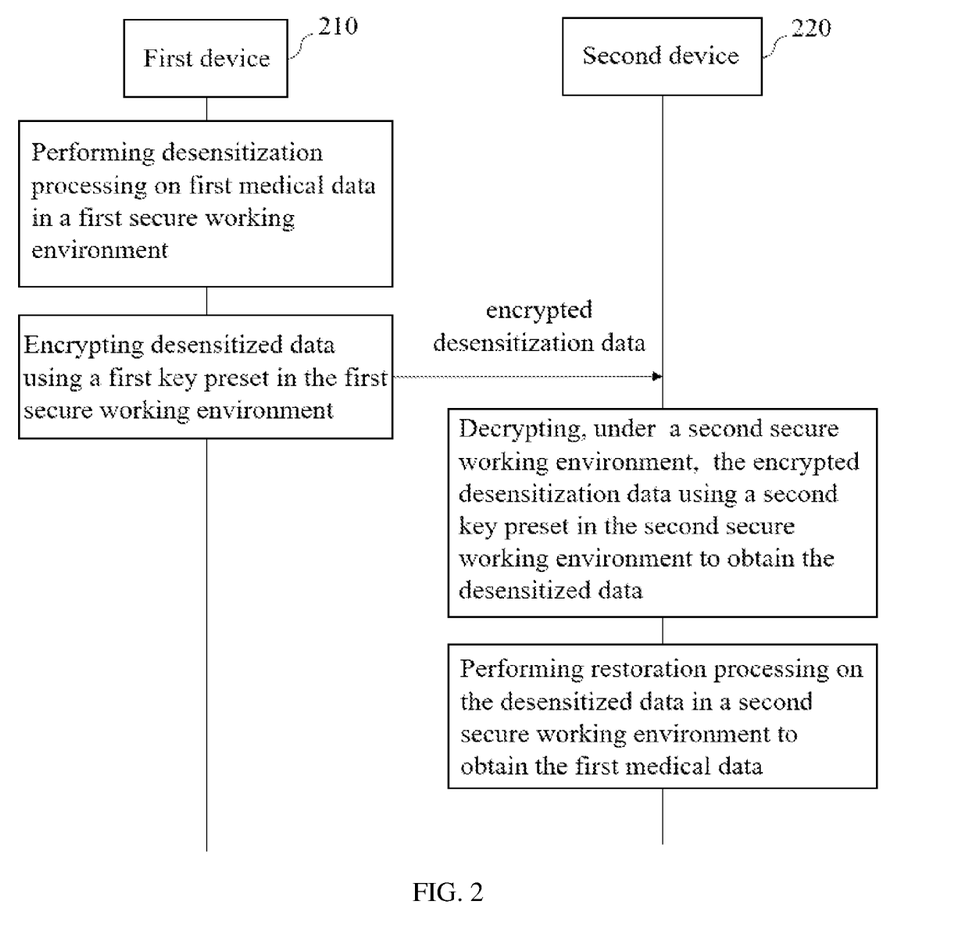
FIG. 2 illustrates a schematic diagram showing data flow of a method for processing medical data according to an embodiment of the disclosure.

FIG. 2 illustrates a schematic diagram showing data flow diagram of a method for processing medical data according to an embodiment of the disclosure. The method is executed by a first device and a second device, the first device and the second device may be implemented by any device with computing and processing capabilities, and the first device and the second device may be computers, mobile phones, etc. The method may include the following steps.

The first device 210 performs desensitization processing on first medical data in a first secure working environment to obtain desensitized data, and provides the desensitized data to the second device. The desensitization processing is preset in the first secure working environment, and the first medical data is stored in the first secure working environment.

The second device 220 performs restoration processing on the desensitized data in a second secure working environment to obtain the first medical data, the restoration processing is preset in the second secure working environment, and the restoration processing corresponds to the desensitization processing.

Specifically, the first device 210 and the second device 220 are both disposed with the secure working environment, and the secure working environment may be implemented by the security sandbox technology, the virtual secure desktop technology, or the virtual working environment created based on the embedded system. Through the above technology, an independent logical storage space may be created in the first device or the second device, to separate applications and stored data running in the secure working environment of the first device or the second device from applications and stored data running in non-secure working environment of the first device or the second device, thereby limiting data communication between the two parties (i.e., the secure working environment and the non-secure working environment), so as to improve the security of the applications and stored data running in the secure working environment.

Through the above technology, both the first device 210 and the second device 220 may be disposed with the secure working environment in their original system. That is, in one implementation, the first device 210 may be disposed with two environments, which are a first secure working environment and a first non-secure working environment. Correspondingly, the second device 220 may be disposed with two environments, which are a second secure working environment and a second non-secure working environment. Taking the first device 210 as an example, the logical isolation between the first secure working environment and the first non-secure working environment in the first device can be realized by the above technology, that is, the operation performed by the first device in the first secure working environment does not affect the data in the first non-secure working environment, and the operation performed by the first device in the first non-secure working environment does not affect the data in the first secure working environment. In this situation, the first non-secure working environment in the first device cannot directly read the data in the first secure working environment, thereby ensuring the security of the data stored in the first secure working environment in the first device to a certain extent.

In one implementation, the first medical data may include sensitive data, for example, including but not limited to personal information, medical information, disease information, past medical history data, etc. In addition, the personal information may include but not limited to name, identity (ID) card number, age and other information, and the medical information may include but not limited to hospital, department, symptom description and other information. Correspondingly, the medical related application may run in the first secure working environment of the first device, and the medical related application may run in the second secure working environment of the second device.

The first medical data may be any medical data stored by the first device 210 in the first secure working environment. The first medical data may include sensitive data. When it is determined that the first device 210 needs to provide data to the outside through the first secure working environment, the first device 210 may perform desensitization processing on the first medical data in the first secure working environment by using the desensitization processing preset in the first secure working environment to obtain desensitized data. Then, the desensitized data is provided to the second device. The first medical data is stored in the first secure working environment.

In one implementation, the first device 210 performs desensitization processing on the first medical data in the first secure working environment, including following steps.

The first device 210 extracts sensitive data from the first medical data, and then performs desensitization processing on the sensitive data. Specifically, when it is determined that the first device needs to provide the first medical data to outside in the first secure working environment, the first device may start the data extraction unit and the data fuzzy processing unit in the first secure working environment, extract the sensitive data from the first medical data by the data extraction unit, and perform desensitization processing on the sensitive data by the data fuzzy process unit.

In one implementation, in order to ensure the integrity of the data stored by the first device in the first secure working environment, after the first device obtains a first instruction transferring data to its outside in the first secure working environment, the first device copies the data corresponding to the first instruction, and takes the copied data as the first medical data.

Figure 3A:
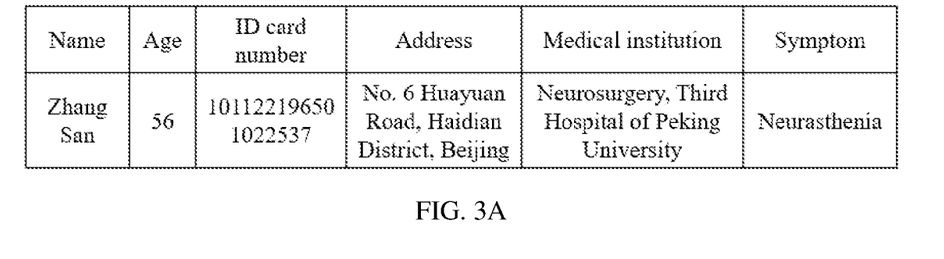
FIG. 3A illustrates a schematic diagram showing first medical data according to an embodiment of the disclosure.
Figure 3B:
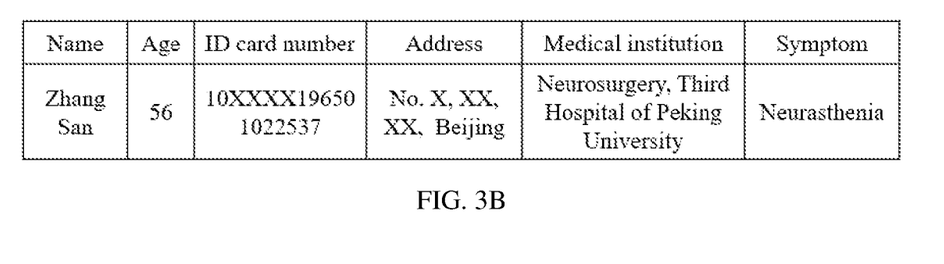
FIG. 3B illustrates a schematic diagram showing desensitized data obtained after desensitization of the first medical data shown in FIG. 3A.

As shown in FIG. 3A, which illustrates a schematic diagram of first medical data provided by an embodiment. Specifically, the first medical data is medical data of one diagnosis and treatment of a patient "Zhang San". As shown in FIG. 3B, which illustrates a schematic diagram of desensitized data obtained after desensitization the first medical data provided in the embodiment. Specifically, the data corresponding to the ID card number and the address in the first medical data are determined as sensitive data, and corresponding desensitization processing is performed. The above example is merely exemplary and is not intended to be limiting. The specific type of sensitive data may be set according to the actual situation. For example, names and ages may also be set as sensitive data. The medical institution, department and symptom description may also be set as sensitive data.

The second device 220 performs restoration processing on the desensitized data to obtain the first medical data by using the restoration processing preset in the second secure working environment. The restoration processing corresponds to the desensitization processing and is used to restore the data after the desensitization processing.

In an exemplary scenario, different data formats may be different. In order to ensure the effective desensitization of data, the format of data may be pre-converted into a preset format, so that the first device can desensitize the data in the preset format in the first secure working environment. In another exemplary scenario, different desensitization processing operations may be set for data in different formats, in this situation, the first device selects a corresponding desensitization processing operation based on the data format in the first secure working environment, and desensitization processing is performed on the data using the corresponding desensitization processing operation.

In this embodiment, the sensitive data of the first medical data is transmitted between the first device and the second device after being hidden and desensitized, and the desensitization processing and the restoration processing are preset in the secure working environments of the devices. The desensitization processing and the restoration processing do not require human intervention, which realizes the protection of sensitive data, improves the portability of data within a certain range, and realizes flexible application of data to a certain extent.

As shown in FIG. 2, in one implementation, in order to better protect of data, the method may further include, after obtaining the desensitized data, the first device encrypts the desensitized data using a first key preset in the first secure working environment to obtain encrypted desensitization data; and the operation of providing the desensitized data to the second device includes providing the encrypted desensitization data to the second device; and decrypting, by the second device, the encrypted desensitized data using a second key preset in the second secure environment under the second secure working environment to obtain the desensitized data.

In this embodiment, in order to better protect the first medical data and avoid its leakage, after the first device 210 obtains the desensitized data, the first device 210 encrypts the desensitized data using the first key preset in the first secure working environment, obtains the encrypted desensitization data, and provides the encrypted desensitization data to the second device. The second device obtains the encrypted desensitization data, and decrypts the encrypted desensitization data using the second key preset in the second secure working environment to obtain the desensitized data.

Specifically, the first key and the second key are keys predetermined by the first device and the second device. The first key and the second key may be the same key, that is, symmetric keys. Correspondingly, the first device may encrypt the desensitized data using a preset symmetric encryption algorithm and the first key; and the second device may decrypt the encrypted desensitization data by using a decryption algorithm corresponding to the preset symmetric encryption algorithm and the second key. Alternatively, the first key and the second key may also be different, that is, asymmetric keys. Correspondingly, the first device may encrypt the desensitized data using a preset asymmetric encryption algorithm and the first key; and the second device may decrypt the encrypted desensitization data by using a decryption algorithm corresponding to the preset asymmetric encryption algorithm and the second key.

In one implementation, the first device may provide the first medical data to the second device through an intranet where the first device and the second device are located. In another implementation, the first device may provide the first medical data to the second device through a mobile storage device.

Specifically, the operation of providing the desensitized data to the second device may include the desensitized data is stored in the mobile storage device, the desensitized data is provided to the second device through the mobile storage device, and the first device and the second device are configured to be capable of running a driver of the mobile storage device only through their secure working environment. Accordingly, in one implementation, the first device is prohibited from running the driver of the mobile storage device in the first non-secure working environment, and the second device is prohibited from running the driver of the mobile storage device in the second non-secure working environment.

Specifically, the mobile storage device may include but are not limited to universal serial bus (USB) disk, mobile hard disk, etc.

In this embodiment, the first device runs the driver of the mobile storage device in the first secure working environment, and the mobile storage device accesses a device interface (also referred to as first device interface) of the first device, that is, after the mobile storage device is connected to the first device, the first device starts a first monitoring process of the device interface. After a first operation of transferring data from the first secure environment to the mobile storage device is monitored by the first monitoring process, the first device copies data corresponding to the first operation to obtain the first medical data, performs desensitization processing on the first medical data in the first secure working environment, obtains desensitized data, and transfers the desensitized data to the mobile storage device.

Subsequently, after the mobile storage device is connected to the second device through a device interface (also referred to as second device interface) of the second device, the second device, in the second secure working environment, monitors a second operation of transferring the desensitized data from the mobile storage device to the second secure working environment by using a started second monitoring process for monitoring the device interface of the second device, and performs restoration processing on the desensitized data in the second secure working environment to obtain the first medical data. The second device may first copy the desensitized data of the mobile storage device, and then perform restoration processing on the copied desensitized data in the second secure working environment to obtain the first medical data. The second device stores the first medical data in the second secure working environment, or the second device displays the first medical data in the second secure working environment.

Specifically, the second device stores the first medical data in the second secure working environment, which may be storing the first medical data in a local storage space accessible by the second device only in the second secure working environment, or storing the first medical data in a cloud storage device accessible by the second device only in the second secure working environment, the cloud storage device and the second device are in the same intranet, and the second device may store the first medical data in the cloud storage device through the intranet under the second secure working environment.

The second device is configured to run the driver of the mobile storage device in the second secure working environment.

In one implementation, the first device and the second device start the first secure working environment and the second secure working environment respectively when they are powered on, and set the device interfaces (i.e., the first device interface and the second device interface) respectively under the first secure working environment and the second secure working environment, to make the first device and the second device can only run the driver of the mobile storage device through their secure working environment. The device interfaces each may be an interface for accessing the mobile storage device.

In one implementation, the first device authenticates the mobile storage device before storing the desensitized data in the mobile storage device. In order to ensure the security of the data stored in the local or connected storage device of the first device, after the first device is connected to the mobile storage device in the first secure working environment, the first device needs to authenticate the mobile storage device before storing the desensitized data in the mobile storage device.

In one mode, the first device may perform identity authentication on the mobile storage device in a password authentication manner. Specifically, one case may be that the first device outputs a password input interface, the password input interface includes a password input area; the first device obtains a first password input from the password input area and performs identity authentication on the mobile storage device with the first password. Specifically, the identity authentication is performed on the mobile storage device according to a judgment result obtained by comparing whether the first password and a pre-stored password are the same, if the judgment result is that the first password is the same as the pre-stored password, it is determined that the identity of the mobile storage device is legal, and the desensitized data can be stored in the mobile storage device; On the contrary, if the judgment result is that the first password is different from the pre-stored password, it is determined that the identity of the mobile storage device is illegal, and the first device prohibits the operation of the mobile storage device, such as prohibiting the driver of the mobile storage device.

Another case may be that the first device reads a second password from a secure storage area of the mobile storage device, and performs identity authentication on the mobile storage device based on the read second password. For the process of identity authentication of the mobile storage device based on the read second password, please refer to the above process of the identity authentication of the mobile storage device using the first password.

In another mode, for the mobile storage device containing a security chip, the mobile storage device may be performed identity authentication in a digital certificate authentication manner. Specifically, the digital certificate stored in the secure storage area of the mobile storage device may be obtained, a device public key corresponding to the mobile storage device may be obtained from a local or corresponding device public key storage server of the first device, the device public key is used to verify the digital certificate. If the digital certificate is verified, the identity of the mobile storage device is determined to be legal, and the desensitized data can be stored in the mobile storage device; and if the digital certificate verification fails to be verified, it is determined that the identity of the mobile storage device is illegal, and the first device prohibits the operation of the mobile storage device, such as prohibiting the driver of the mobile storage device.

In one implementation, the second device may be further configured to read the desensitized data from the mobile storage device after determining a login account having a permission to read the mobile storage device in the second secure working environment.

In this embodiment, in order to ensure the security of the data better, the second device reads the desensitized data from the mobile storage device after determining the login account having the permission to read the mobile storage device in the second secure working environment, and then executes the subsequent steps.

It can be understood that the first device and the second device may also correspond to a permission management server for setting the data permissions of the first device and the second device in their secure working environment. The permission management server may set data permissions for the accounts logged in by the first device and the second device in their secure working environment. For example, the second device can read the desensitized data from the mobile storage device only after determining the login account having the permission to read the mobile storage device in the second secure working environment, and then perform the subsequent steps.

For example, the above desensitized data may be encrypted desensitization data. After the second device determines the login account having the permission to read the mobile storage device in the second secure working environment, the reading the desensitized data from the mobile storage device may include decrypting the encrypted desensitization data using a second key preset in the second secure environment to obtain the desensitized data. Further, the second device can restore the desensitized data only after determining the login account having the permission to read the data plaintext in the second secure working environment. That is, in another implementation, after the second device determines the login account without the permission to read the data plaintext in the second secure working environment, the second device does not perform the operation of restoration processing of the desensitized data in the second secure working environment. Accordingly, the second device may view and/or store the decrypted desensitization data in the second secure working environment.

In one situation, whether the login account of the second device in the second secure working environment has the permission to decrypt the data may be set, and only when the second device determines that the login account of the second device in the second secure working environment has the permission to decrypt the data, the second device may decrypt the encrypted desensitization data by using the second key preset in the second secure working environment. If the second device determines that the login account does not have the decryption permission in the second secure working environment, the second device does not perform the operation of decrypting the encrypted desensitization data using the second key preset in the second secure environment.

In one implementation of this embodiment, taking the first device as an example, the first device may send a permission configuration request (also referred to as authority configuration request) to the permission management server for its currently logged in account in the first secure working environment. The permission management server may set corresponding permission to the currently logged in account of the first device based on the permission configuration request, generate a permission configuration reply, and feed back the permission configuration reply to the first device. The first device obtains the permission configuration reply fed back by the permission management server based on the permission configuration request in the first secure working environment, and set the permission of the currently logged in account based on the permission configuration reply.

Similarly, the second device may request permission configuration from the permission management server according to the above process when there is a requirement for permission configuration.

In this embodiment, the corresponding mobile storage device can only be identified under a specific secure working environment, and the account and mobile storage device logged in to the secure working environment need to be authorized, and thus the whole medical data processing process is secure and controllable. In addition, the medical data is desensitized and encrypted, which facilitates the sharing of medical data within a certain controlled range and realizes the protection of sensitive data in medical data.

Figure 4:
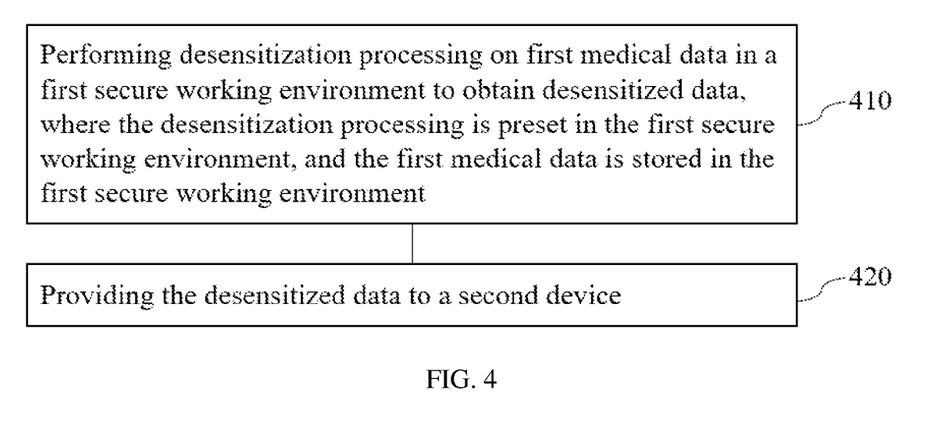
FIG. 4 illustrates a schematic flowchart of a method for processing medical data according to an embodiment of the disclosure.

Corresponding to the above method embodiments, an embodiment of the disclosure provides a method for processing medical data, which is executed by a first device. As shown in FIG. 4, the method may include the following steps 410 to 420 (abbreviated as S410 to S420).

S410, performing desensitization processing on first medical data in a first secure working environment to obtain desensitized data. The desensitization processing is preset in the first secure working environment, and the first medical data is stored in the first secure working environment.

S420, providing the desensitized data to a second device.

In one implementation, before the S420, the method further includes encrypting the desensitized data using a first key preset in the first secure working environment to obtain encrypted desensitization data. Accordingly, in the S420, the encrypted desensitization data is provided to the second device.

In one implementation, in the S420, the desensitized data is stored in a mobile storage device, and the desensitized data is provided to the second device through the mobile storage device. The first device and the second device are configured to be capable of running a driver of the mobile storage device only through their secure working environment.

In one implementation, the method further includes starting the first secure working environment when the first device is powered on, and setting a device interface under the first secure working environment so that the first device is set to be capable of running the driver of the mobile storage device only through the first secure working environment. The device interface is an interface for the first device to access the mobile storage device.

In one implementation, the method further includes performing identity authentication on the mobile storage device before storing the desensitized data in the mobile storage device. For the specific identity authentication method, please refer to the above embodiment of the method for processing medical data executed by the first device and the second device.

In one implementation, the S410 of the method includes: extracting sensitive data from the first medical data, and then perform desensitization processing on the sensitive data.

Figure 5:
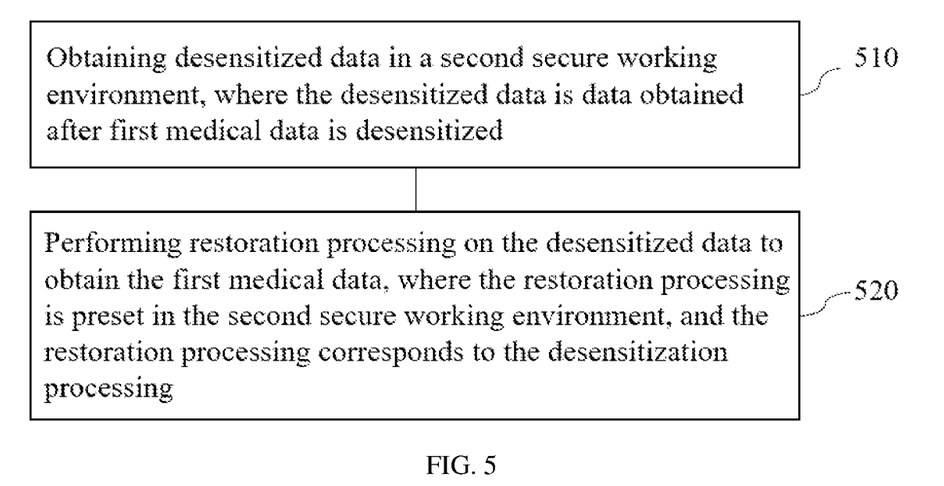
FIG. 5 illustrates a schematic flowchart of a method for processing medical data according to another embodiment of the disclosure.

Corresponding to the above method embodiments, an embodiment of the disclosure provides a method for processing medical data, which is executed by a second device. As shown in FIG. 5, the method may include the following steps 510 to 520 (abbreviated as S510 to S520).

S510, obtaining desensitized data in a second secure working environment, where the desensitized data is data obtained after first medical data is desensitized.

S520, performing restoration processing on the desensitized data to obtain the first medical data, where the restoration processing is preset in the second secure working environment, and the restoration processing corresponds to the desensitization processing.

In one implementation, the desensitized data is encrypted desensitization data. Accordingly, the S510 of the method further includes: decrypting the encrypted desensitization data using a second key preset in the second secure working environment to obtain desensitized data.

In one implementation, in the S510, in the second secure working environment, the desensitized data is obtained by the second device through a connected mobile storage device, and the second device is configured to be capable of running the driver of the mobile storage device only through the second secure working environment.

In one implementation, the second secure working environment is started when the second device is powered on, and a device interface of the second device is set under the second secure working environment, so that the second device is set to be capable of running the driver of the mobile storage device only through the second secure working environment. Specifically, the device interface is an interface for the second device to access the mobile storage device.

In one implementation, when the mobile storage device accesses the device interface of the second device, the mobile storage device is performed identity authentication. For the specific identity authentication method, please refer to the above embodiment of the method for processing medical data executed by the first device and the second device.

In one implementation, in the S510, after determining a login account having a permission to read the mobile storage device in the second secure working environment, the desensitized data is read from the mobile storage device.

Figure 6:
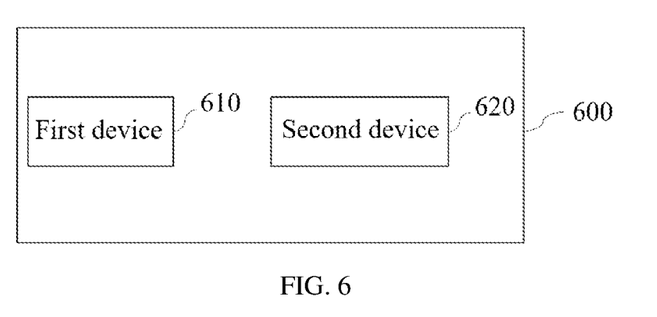
FIG. 6 illustrates a schematic block diagram of a system for processing medical data according to an embodiment of the disclosure.

Corresponding to the above method embodiments, an embodiment of the disclosure provides a system 600 for processing medical data, which includes a first device 610 and a second device 620, as shown in FIG. 6.

The first device 610 is configured to perform desensitization processing on first medical data in a first secure working environment of the first device to obtain desensitized data, and provide the desensitized data to the second device 620. The desensitization processing is preset in the first secure working environment, and the first medical data is stored in the first secure working environment.

The second device 620 is configured to perform restoration processing on the desensitized data in a second secure working environment of the second device to obtain the first medical data, in which the restoration processing is preset in the second secure working environment, and the restoration processing corresponds to the desensitization processing.

The foregoing describes specific embodiments of the disclosure, and other embodiments are within the scope of the appended claims. In some cases, operations or steps recited in the appended claims can be performed in a different order from those in the embodiments, and the desired results can still be achieved. In addition, the processes illustrated in the accompanying drawings do not have to follow the specific order or continuous order to achieve the desired results. In some embodiments, multitasking and parallel processes are also possible or may be advantageous.

Figure 7:
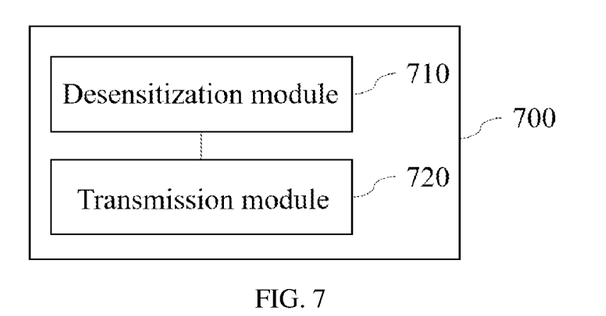
FIG. 7 illustrates a schematic block diagram of an apparatus for processing medical data according to an embodiment of the disclosure.

Corresponding to the above method embodiments, an embodiment of the disclosure provides a device 700 for processing medical data, which is provided in a first device. A schematic block diagram is shown in FIG. 7, the device 700 includes:

a desensitization module 710, configured to perform desensitization processing on first medical data in a first secure working environment to obtain desensitized data, the desensitization processing being preset in the first secure working environment, and the first medical data being stored in the first secure working environment; and a transmission module 720, configured to provide the desensitized data to a second device.

Figure 8:
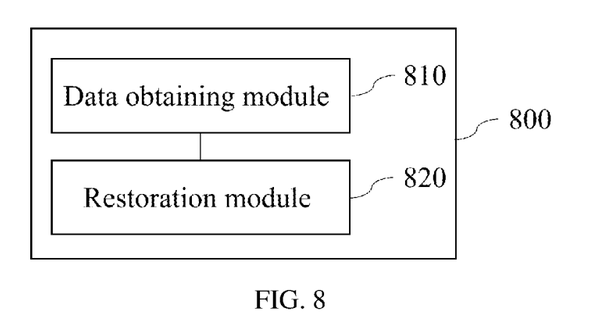
FIG. 8 illustrates a schematic block diagram of an apparatus for processing medical data according to another embodiment of the disclosure.

Corresponding to the above method embodiments, an embodiment of the disclosure provides a device 800 for processing medical data, which is provided in a second device. A schematic block diagram is shown in FIG. 8, the device 800 includes:

a data obtaining module 810, configured to obtain desensitized data in a second secure working environment, and the desensitized data being data obtained after first medical data is performed desensitization processing; and a restoration module 820, configured to perform restoration processing on the desensitized data to obtain the first medical data, the restoration processing being preset in the second secure working environment, and the restoration processing corresponding to the desensitization processing.

The above device embodiments correspond to the method embodiments, and the specific description can be referred to the description of the method embodiments of the method, which will not be repeated here. The device embodiment is obtained based on the corresponding method embodiment and has the same technical effects as the corresponding method embodiment, the specific description can be referred to the corresponding method embodiment.

An embodiment of the disclosure also provides a computer-readable storage medium on which computer programs are stored, and the computer programs are configured to be executed in a computer to make the computer to execute the method for processing medical data on a side of the first device provided in the disclosure.

An embodiment of the disclosure also provides a computing device, including a memory and a processor, executable codes are stored in the memory, and the processor is configured to execute the executable codes to implement the method for processing medical data on the side of the first device provided in the disclosure.

An embodiment of the disclosure also provides a computer-readable storage medium on which computer programs are stored, and the computer programs are configured to be executed in a computer to make the computer to execute the method for processing medical data on a side of the second device provided in the disclosure.

An embodiment of the disclosure also provides a computing device, including a memory and a processor, executable codes are stored in the memory, and the processor is configured to execute the executable codes to implement the method for processing medical data on the side of the second device provided in the disclosure.

The embodiments in the disclosure are described in a progressive manner, same and similar parts between the embodiments can be referred to each other, and each embodiment focuses on differences from other embodiments. In particular, since the embodiments of the storage medium and the computing device are substantially similar to the embodiments of the method, the description is relatively simple. For related parts, reference may be made to some descriptions of the method embodiments.

Those skilled in the art will realize that in the one or more embodiments above, the functions described in the embodiments of the disclosure may be implemented by hardware, software, firmware or any combination thereof. When implemented in software, these functions may be stored or transmitted as one or more instructions or codes in a computer-readable medium.

Objectives, technical solutions and beneficial effects of the embodiments of the disclosure are further described in detail through the specific embodiments above. It should be understood that the foregoing descriptions are merely specific implementations of the embodiments of the disclosure, and are not intended to limit the scope of protection of the disclosure. Any modification, equivalent substitution, improvement, etc. made on the basis of the technical solutions of the disclosure should be included in the scope of protection of the disclosure.

What is claimed is:

1. A method for processing medical data, executed by a first device and a second device, comprising:
    starting, by the first device, a first monitoring process of a first device interface after a mobile storage device being connected to the first device is monitored;
    copying, by the first device, data corresponding to a first operation to obtain first medical data after the first operation of transferring the data from a first secure working environment to the mobile storage device is monitored by the first monitoring process;
    performing, by the first device, desensitization processing on the first medical data in the first secure working environment to obtain desensitized data; and
    storing, by the first device, the desensitized data in the mobile storage device, and then providing the desensitized data to the second device through the mobile storage device; wherein the first device is disposed with the first secure working environment and a first non-secure working environment logically isolated with each other, the second device is disposed with a second secure working environment and a second non-secure working environment logically isolated with each other; the first device is configured to start the first secure working environment when the first device is powered on to set the first device interface under the first secure working environment, the second device is configured to start the second secure working environment when the second device is powered on to set a second device interface under the second secure working environment, thereby the first device and the second device are capable of running a device driver of the mobile storage device only through the first secure working environment and the second secure working environment respectively; and the desensitization processing is preset in the first secure working environment, and the first medical data is stored in the first secure working environment; and
    performing, by the second device, restoration processing on the desensitized data in the second secure working environment to obtain the first medical data, wherein the restoration processing is preset in the second secure working environment, and the restoration processing corresponds to the desensitization processing.

2. The method according to claim 1, further comprising:
    encrypting, by the first device, the desensitized data using a first key preset in the first secure working environment after obtaining the desensitized data, to obtain encrypted desensitization data;
    wherein the providing the desensitized data to the second device comprises:
        providing the encrypted desensitization data to the second device; and
        decrypting, by the second device, the encrypted desensitization data using a second key preset in the second secure working environment to obtain the desensitized data.

3. The method according to claim 1, further comprising: performing, by the first device, identity authentication on the mobile storage device before the storing, by the first device, the desensitized data in the mobile storage device.

4. The method according to claim 1, wherein the performing, by the first device, desensitization processing on the first medical data in the first secure working environment comprises:
    extracting, by the first device, sensitive data from the first medical data; and
    performing, by the first device, the desensitization processing on the sensitive data.

5. The method according to claim 1, further comprising: reading, by the second device, the desensitized data from the mobile storage device after determining a login account having a permission to read the mobile storage device in the second secure working environment.

6. A method for processing medical data, executed by a first device, comprising:
    starting a first monitoring process of a first device interface after a mobile storage device being connected to the first device is monitored; copying data corresponding to a first operation to obtain first medical data after the first operation of transferring data from a first secure working environment to the mobile storage device is monitored by the first monitoring process; and preforming desensitization processing on the first medical data in the first secure working environment to obtain desensitized data; wherein the desensitization processing is preset in the first secure working environment, and the first medical data is stored in the first secure working environment; and
    storing the desensitized data in the mobile storage device, and then providing the desensitized data to a second device through the mobile storage device, wherein the first device is disposed with the first secure working environment and a first non-secure working environment logically isolated with each other, the second device is provided with a second secure working environment and a second non-secure working environment logically isolated with each other; the first device is configured to start the first secure working environment when the first device is powered on to set the first device interface under the first secure working environment, the second device is configured to start the second secure working environment when the second device is powered on to set a second device interface under the second secure working environment, thereby the first device and the second device are capable of running a device driver of the mobile storage device only through the first secure working environment and the second secure working environment respectively.

7. A system for processing medical data, comprising a first device and a second device;
    wherein the first device is configured to start a first monitoring process of a first device interface after a mobile storage device being connected to the first device is monitored; copy data corresponding to a first operation to obtain first medical data after the first operation of transferring the data from a first secure working environment to the mobile storage device is monitored by the first monitoring process; perform desensitization processing on the first medical data in the first secure working environment to obtain desensitized data; store the desensitized data in the mobile storage device, and then providing the desensitized data to the second device through the mobile storage device; the first device is disposed with the first secure working environment and a first non-secure working environment logically isolated with each other, the second device is disposed with a second secure working environment and a second non-secure working environment logically isolated with each other; the first device is configured to start the first secure working environment when the first device is powered on to set the first device interface under the first secure working environment, the second device is configured to start the second secure working environment when the second device is powered on to set a second device interface under the second secure working environment, thereby the first device and the second device are capable of running a device driver of the mobile storage device only through the first secure working environment and the second secure working environment respectively, the desensitization processing is preset in the first secure working environment, and the first medical data is stored in the first secure working environment;

wherein the second device is configured to perform restoration processing on the desensitized data in the second secure working environment to obtain the first medical data; the restoration processing is preset in the second secure working environment, and the restoration processing corresponds to the desensitization processing.

\* \* \* \* \*